US012339279B2

(12) United States Patent
Jensen et al.

(10) Patent No.: US 12,339,279 B2
(45) Date of Patent: Jun. 24, 2025

(54) METHOD OF DETERMINING AN IMMUNOGENIC RESPONSE CHARACTERISTIC OF A CHEMICAL SUBSTANCE

(71) Applicant: FIDA BIOSYSTEMS APS, Søborg (DK)

(72) Inventors: Henrik Jensen, Søborg (DK); Morten Enghave Pedersen, Søborg (DK)

(73) Assignee: FIDA BIOSYSTEMS APS, Søborg (DK)

( * ) Notice: Subject to any disclaimer, the term of this patent is extended or adjusted under 35 U.S.C. 154(b) by 0 days.

(21) Appl. No.: 18/585,679

(22) Filed: Feb. 23, 2024

(65) Prior Publication Data
US 2024/0192207 A1   Jun. 13, 2024

Related U.S. Application Data

(63) Continuation of application No. PCT/DK2022/050172, filed on Aug. 23, 2022.

(30) Foreign Application Priority Data

Aug. 24, 2021   (DK) .............................. PA 202100831

(51) Int. Cl.
*G01N 33/53* (2006.01)
*G01N 33/50* (2006.01)
*G01N 33/564* (2006.01)

(52) U.S. Cl.
CPC ....... *G01N 33/564* (2013.01); *G01N 33/5008* (2013.01); *G01N 2800/24* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,310,359 B2 | 4/2016 | Jensen et al. | |
| 2013/0059313 A1* | 3/2013 | Jensen | G16B 45/00 435/7.1 |
| 2013/0344621 A1* | 12/2013 | Wang | G01N 33/94 436/501 |
| 2017/0285023 A1 | 10/2017 | Barbosa | |
| 2023/0258644 A1* | 8/2023 | Marks | G01N 33/54388 436/506 |

FOREIGN PATENT DOCUMENTS

| | | |
|---|---|---|
| CN | 113109572 A | 7/2021 |
| WO | 9839656 | 9/1998 |
| WO | 2021046316 A2 | 3/2021 |
| WO | 2021180289 A1 | 9/2021 |

OTHER PUBLICATIONS

Pedersen et al., Flow-induced Dispersion Analysis (FIDA) for Protein Quantification and Characterization, Methods in Molecular Biology, Chapter 8, Mar. 8, 2019, pp. 109-123. (Year: 2019).*
US Department of Health and Human Services, Food and Drug Administration: "Guidance for Industry. Immunogenicity Assessment for Therapeutic Protein Products", Aug. 2014 (39 pages).
Nygaard et al., An efficient method for estimating the hydrodynamic radius of disordered protein conformations, Biophysical Journal, 113, 550-557, Aug. 8, 2017 (8 page).
Valor, "Understanding the Immunogenicity Concept", Reumatol Clin. 2013;9(1):1-4 (4 pages).
Poulsen, N. N. et al., "Flow-induced dispersion analysis for probing anti-dsDNA antibody binding heterogeneity in systemic lupus erythematosus patients: Toward a new approach for diagnosis and patient stratification", Analytical Chemistry, 2016, 88.18: 9056-9061 (10 pages).
Pedersen, M. E., et al., "Size-based characterization of adalimumab and TNF-α interactions using flow induced dispersion analysis: assessment of avidity-stabilized multiple bound species", Scientific Reports, 2021, 11.1: 1-10 (10 pages).
Fidabio, Flow Induced Dispersion Analysis. Product description [online]. Bucher biotec [retrieved on May 21, 2024 using web.archive.org dated Jan. 13, 2021]. Retrieved from the internet <URL: https://web.archive.org/web/20210113070040/https://www.bucher.ch/products/FIDA_Fidalyzer.html> (8 pages).
Lavoisier, A et al.: "Early developability screen of therapeutic antibody . . . ", MABS, 2015, vol. 7, No. 1 (8 pages).
Pedersen, ME et al., "Assessment of immunogenicity and drug activity in patient sera by flow-induced dispersion analysis", Scientific Reports, 2022, 12.1: 1-10 (10 pages).

(Continued)

*Primary Examiner* — Gary Counts
(74) *Attorney, Agent, or Firm* — Boone IP Law

(57) ABSTRACT

A method for determining an immunogenic response characteristic of a chemical substance. The method includes obtaining a biological liquid sample including the chemical substance, providing at least one prepared sample from at least a portion of the biological liquid sample, for each prepared sample, subjecting the at least a test portion of the prepared sample to a flow involving that the test portion of the prepared sample is in contact with a binding partner for the chemical substance, wherein the binding partner includes an optical marker, performing at least one read out of the optical marker and based thereon, determining a characteristic flow parameter of the marked binding partner in contact with the prepared sample and comparing the determined characteristic flow parameter with a respective reference value and determining the immunogenic response characteristic of the chemical substance.

19 Claims, 8 Drawing Sheets

(56) References Cited

OTHER PUBLICATIONS

International Search Report and Written Opinion of the International Searching Authority mailed on Oct. 24, 2022 in PCT/DK2022/050172 by the Nordic Patent Institute (11 pages).
Examination Report mailed on May 12, 2022 by the Danish Patent and Trademark Office in PA 2021 00831 (10 pages).

* cited by examiner

Fig. 6

| Patient no. | Apparent $R_a$ (nm) of TNF-α-AF488 as function of serum dilution (% v/v) | | | | | | | Assessment |
|---|---|---|---|---|---|---|---|---|
| | 0.01 | 0.1 | 1 | 5 | 10 | 15 | 20 | 40 | |
| 1 (ctrl) | 3.08 ±0.04 | 3.04 ±0.02 | 3.03 ±0.02 | 2.92 ±0.12 | 3.09 ±0.04 | 3.01 ±0.02 | 3.03 ±0.03 | 2.87 ±0.34 | As expected - no binding |
| 2 (ctrl) | 3.11 ±0.02 | 2.79 ±0.03 | 2.85 ±0.03 | 2.80 ±0.16 | 2.76 ±0.04 | 2.99 ±0.03 | 3.08 ±0.05 | 3.06 ±0.03 | As expected - no binding |
| 3 (ctrl) | 3.11 ±0.06 | 3.22 ±0.03 | 3.18 ±0.03 | 3.26 ±0.10 | 3.21 ±0.06 | 3.04 ±0.08 | 3.33 ±0.07 | 3.11 ±0.05 | As expected - no binding |
| 4 (ctrl) | 3.02 ±0.01 | 3.03 ±0.01 | 3.02 ±0.01 | 3.09 ±0.10 | 3.09 ±0.02 | 2.93 ±0.07 | 3.26 ±0.05 | 3.22 ±0.05 | As expected - no binding |
| 5 (ctrl) | 3.29 ±0.03 | 3.06 ±0.02 | 3.05 ±0.02 | 3.05 ±0.01 | 3.09 ±0.11 | 3.27 ±0.01 | 3.11 ±0.02 | 3.23 ±0.03 | As expected - no binding |
| 6 (ctrl) | 3.23 ±0.05 | 3.33 ±0.05 | 3.28 ±0.00 | 3.25 ±0.06 | 3.03 ±0.01 | 3.29 ±0.04 | 3.35 ±0.01 | 3.49 ±0.05 | Other TNF inhibitor |
| 7 (ctrl) | 3.12 ±0.03 | 3.31 ±0.04 | 3.31 ±0.01 | 3.71 ±0.04 | 4.92 ±0.02 | 5.65 ±0.03 | 5.59 ±0.21 | 5.32 ±0.23 | Other TNF inhibitor |
| 8 (ctrl) | 3.16 ±0.09 | 3.28 ±0.09 | 3.33 ±0.01 | 3.68 ±0.10 | 4.49 ±0.08 | 5.20 ±0.21 | 5.92 ±0.10 | 7.30 ±0.57 | Other TNF inhibitor |
| 9 (ctrl) | 3.27 ±0.13 | 3.23 ±0.05 | 3.32 ±0.02 | 3.95 ±0.02 | 4.72 ±0.16 | 5.46 ±0.05 | 6.27 ±0.19 | 7.33 ±0.62 | Other TNF inhibitor |
| 10 (ctrl) | 3.22 ±0.03 | 3.31 ±0.01 | 3.44 ±0.01 | 4.63 ±0.07 | 6.56 ±0.06 | 7.45 ±0.05 | 8.16 ±0.10 | 9.01 ±0.45 | Other TNF inhibitor |
| 11 | 2.91 ±0.03 | 2.71 ±0.12 | 2.76 ±0.07 | 2.99 ±0.03 | 3.07 ±0.03 | 3.04 ±0.03 | 3.61 ±0.12 | 4.05 ±0.31 | Neutralizing antibodies |
| 12 | 3.26 ±0.00 | 3.25 ±0.02 | 3.25 ±0.02 | 3.29 ±0.01 | 3.38 ±0.02 | 3.35 ±0.13 | 3.52 ±0.07 | 3.49 ±0.07 | Neutralizing antibodies |
| 13 | 3.27 ±0.01 | 3.27 ±0.01 | 3.31 ±0.05 | 3.49 ±0.09 | 3.57 ±0.03 | 3.67 ±0.05 | 3.83 ±0.04 | 4.57 ±0.14 | Neutralizing antibodies |
| 14 | 3.20 ±0.02 | 3.28 ±0.04 | 3.75 ±0.03 | 3.41 ±0.03 | 3.51 ±0.01 | 3.85 ±0.01 | 3.77 ±0.03 | 4.68 ±0.35 | Neutralizing antibodies |
| 15 | 3.21 ±0.10 | 3.23 ±0.01 | 3.30 ±0.02 | 3.44 ±0.01 | 3.69 ±0.03 | 3.94 ±0.01 | 4.29 ±0.03 | 5.29 ±0.43 | Neutralizing antibodies |
| 16 | 3.25 ±0.08 | 3.32 ±0.08 | 3.33 ±0.09 | 3.44 ±0.03 | 3.56 ±0.05 | 3.47 ±0.05 | 3.86 ±0.03 | 4.21 ±0.02 | Neutralizing antibodies |
| 17 | 3.20 ±0.04 | 3.29 ±0.04 | 3.22 ±0.01 | 3.43 ±0.03 | 3.63 ±0.03 | 3.75 ±0.05 | 4.00 ±0.06 | 5.07 ±0.26 | Neutralizing antibodies |
| 18 | 3.18 ±0.03 | 3.08 ±0.04 | 3.17 ±0.04 | 3.49 ±0.41 | 4.25 ±0.09 | 4.91 ±0.03 | 5.65 ±0.28 | 7.95 ±0.51 | Normal drug response |
| 19 | 3.03 ±0.07 | 3.18 ±0.01 | 3.33 ±0.03 | 3.61 ±0.04 | 4.07 ±0.05 | 4.68 ±0.05 | 4.97 ±0.20 | 6.41 ±0.34 | Normal drug response |
| 20 | 3.22 ±0.04 | 3.24 ±0.03 | 3.32 ±0.02 | 3.85 ±0.01 | 4.04 ±0.04 | 4.76 ±0.08 | 5.21 ±0.21 | 6.18 ±0.10 | Normal drug response |
| 21 | 3.21 ±0.04 | 3.11 ±0.02 | 3.22 ±0.02 | 3.72 ±0.03 | 4.29 ±0.10 | 5.05 ±0.04 | 5.73 ±0.14 | 6.29 ±0.17 | Normal drug response |
| 22 | 3.12 ±0.06 | 3.38 ±0.03 | 3.22 ±0.07 | 3.75 ±0.04 | 4.28 ±0.02 | 4.79 ±0.25 | 5.69 ±0.03 | 8.02 ±0.52 | Normal drug response |
| 23 | 3.11 ±0.04 | 3.11 ±0.03 | 3.28 ±0.03 | 4.16 ±0.03 | 4.18 ±0.22 | 4.54 ±0.01 | 5.34 ±0.17 | 7.59 ±0.31 | Normal drug response |
| 24 | 3.12 ±0.03 | 3.29 ±0.01 | 3.28 ±0.02 | 3.75 ±0.02 | 4.33 ±0.06 | 4.92 ±0.05 | 5.38 ±0.19 | 7.15 ±0.36 | Normal drug response |
| 25 | 3.13 ±0.03 | 3.20 ±0.03 | 3.25 ±0.03 | 3.84 ±0.03 | 4.48 ±0.05 | 5.08 ±0.06 | 5.76 ±0.11 | 7.42 ±0.64 | Normal drug response |
| 26 | 3.19 ±0.02 | 3.24 ±0.09 | 3.36 ±0.02 | 3.75 ±0.01 | 4.77 ±0.05 | 5.07 ±0.07 | 6.20 ±0.08 | 7.13 ±0.40 | Normal drug response |
| 27 | 2.93 ±0.04 | 3.29 ±0.10 | 3.23 ±0.11 | 3.95 ±0.04 | 4.69 ±0.04 | 5.49 ±0.06 | 5.92 ±0.33 | 6.88 ±0.34 | Normal drug response |
| 28 | 3.09 ±0.06 | 3.31 ±0.03 | 3.32 ±0.10 | 4.09 ±0.05 | 4.81 ±0.05 | 5.64 ±0.10 | 6.33 ±0.12 | 8.10 ±0.22 | Normal drug response |
| 29 | 3.22 ±0.04 | 3.32 ±0.02 | 3.41 ±0.05 | 4.03 ±0.04 | 4.93 ±0.07 | 5.81 ±0.10 | 6.46 ±0.15 | 7.32 ±0.45 | Normal drug response |
| 30 | 3.29 ±0.00 | 3.16 ±0.02 | 3.41 ±0.02 | 4.64 ±0.02 | 4.68 ±0.02 | 5.80 ±0.11 | 6.49 ±0.11 | 6.66 ±0.23 | Normal drug response |
| 31 | 3.08 ±0.02 | 3.27 ±0.01 | 3.20 ±0.04 | 4.72 ±0.05 | 5.66 ±0.10 | 6.21 ±0.33 | 7.42 ±0.09 | 9.42 ±1.04 | Non-neutralizing antibodies |
| 32 | 3.16 ±0.02 | 3.18 ±0.04 | 3.17 ±0.07 | 4.27 ±0.01 | 5.43 ±0.06 | 5.81 ±0.03 | 5.77 ±0.07 | 5.95 ±0.32 | Mixed mode |
| 33 | 3.18 ±0.02 | 3.27 ±0.05 | 3.36 ±0.10 | 4.29 ±0.04 | 5.46 ±0.10 | 6.30 ±0.10 | 7.09 ±0.86 | 8.23 ±0.43 | Non-neutralizing antibodies |
| 34 | 2.98 ±0.04 | 3.04 ±0.05 | 3.09 ±0.05 | 4.48 ±0.06 | 5.78 ±0.38 | 6.86 ±0.05 | 7.62 ±0.13 | 8.68 ±0.20 | Non-neutralizing antibodies |
| 35 | 3.24 ±0.02 | 3.12 ±0.03 | 3.23 ±0.03 | 4.48 ±0.01 | 6.02 ±0.10 | 6.95 ±0.10 | 7.38 ±0.12 | 7.05 ±0.79 | Non-neutralizing antibodies |
| 36 | 3.29 ±0.03 | 3.07 ±0.02 | 3.18 ±0.18 | 4.63 ±0.66 | 5.77 ±0.39 | 7.67 ±0.29 | 7.61 ±0.37 | 7.05 ±0.23 | Non-neutralizing antibodies |
| 37 | 3.23 ±0.05 | 3.27 ±0.05 | 3.44 ±0.02 | 4.72 ±0.05 | 6.02 ±0.08 | 6.95 ±0.08 | 7.72 ±0.12 | 9.59 ±0.95 | Non-neutralizing antibodies |
| 38 | 3.24 ±0.03 | 3.37 ±0.03 | 3.50 ±0.04 | 4.83 ±0.07 | 6.53 ±0.08 | 7.53 ±0.05 | 8.25 ±0.07 | 9.73 ±0.58 | Non-neutralizing antibodies |
| 39 | 3.05 ±0.19 | 3.11 ±0.05 | 3.62 ±0.05 | 4.93 ±0.23 | 6.53 ±0.06 | 7.26 ±0.08 | 7.45 ±0.25 | 9.53 ±0.62 | Non-neutralizing antibodies |
| 40 | 3.24 ±0.06 | 3.12 ±0.01 | 3.57 ±0.05 | 5.23 ±0.05 | 6.70 ±0.10 | 7.86 ±0.09 | 2.30 ±0.09 | 8.35 ±0.60 | Non-neutralizing antibodies |
| Benchmark | 3.28 | 3.28 | 3.37 | 3.78 | 4.38 | 5.04 | 5.83 | 7.24 | Std. curve in 20 % plasma |

Fig. 8

| Patient no. | Drug response factor (DRF) (% v/v serum) | DRF normalized (DRF$_{Norm}$) | Goodness of fit (R$^2$) |
|---|---|---|---|
| Benchmark ±50 % | 3,190 0.90-14.70 | 1,000 0.28-4.61 | 1,000 0.98-0.98 |
| 11 | 116,668 | 36,573 | 0.230 |
| 12 | 273,219 | 85,649 | 0.760 |
| 13 | 42,178 | 13,222 | 0.980 |
| 14 | 40,133 | 12,581 | 0.811 |
| 15 | 19,918 | 6,244 | 0.984 |
| 16 | 67,134 | 21,045 | 0.942 |
| 17 | 26,707 | 8,372 | 0.959 |
| 18 | 2,491 | 0.781 | 0.971 |
| 19 | 7,061 | 2,214 | 0.990 |
| 20 | 7,187 | 2,253 | 0.987 |
| 21 | 5,134 | 1,609 | 0.951 |
| 22 | 2,384 | 0.747 | 0.972 |
| 23 | 3,704 | 1,161 | 0.960 |
| 24 | 3,909 | 1,225 | 0.996 |
| 25 | 2,774 | 0.869 | 0.998 |
| 26 | 2,089 | 0.655 | 0.968 |
| 27 | 2,898 | 0.909 | 0.952 |
| 28 | 1,178 | 0.369 | 0.993 |
| 29 | 1,083 | 0.339 | 0.990 |
| 30 | 0.768 | 0.241 | 0.985 |
| 31 | 0.257 | 0.081 | 0.965 |
| 32 | 4,037 | 1,265 | 0.692 |
| 33 | 0.302 | 0.095 | 0.964 |
| 34 | 0.118 | 0.037 | 0.943 |
| 35 | 0.298 | 0.093 | 0.797 |
| 36 | 0.088 | 0.028 | 0.921 |
| 37 | 0.072 | 0.023 | 0.905 |
| 38 | 0.013 | 0.004 | 0.845 |
| 39 | 0.094 | 0.030 | 0.836 |
| 40 | 0.013 | 0.004 | 0.787 |

Patients 11–17: NAb positive
Patients 18–29: Normal responders
Patients 30–40: Non-NAb positive

METHOD OF DETERMINING AN IMMUNOGENIC RESPONSE CHARACTERISTIC OF A CHEMICAL SUBSTANCE

TECHNICAL FIELD

The invention relates to a method of determining a response characteristic of a drug comprising a chemical substance.

BACKGROUND ART

Chemical substances, such as pharmaceuticals and especially biopharmaceuticals have become an increasingly important class of therapeutic drugs since they provide major benefits in the treatment of many severe diseases such as autoimmune diseases, cancer and diabetes. The primary advantages amount to high specificity and effective replacement or substitution of endogenous compounds (e.g. insulin and erythropoietin). However, therapeutic effect of chemical substances, such as biopharmaceuticals may differ from individual to individual. Thus, monitoring of individuals may be needed to measure the therapeutic drug concentration in individuals as well as to monitor the onset unwanted immunogenic response against the treatment, formally known as immunogenicity.

The consequences of immunogenicity range from no considerable adverse effects to severe side effects such as reduced treatment efficacy and even anaphylaxis. In addition, immunogenic reactions for a given individual may change over time, e.g. over a treatment program over lifetime, over a hormone related cycle and/or in dependence of physical and/or psychological state of the individual.

Biologically, this may manifest through the generation and/or presence of circulating anti-drug-antibodies (ADA). The ADA includes neutralizing antibodies (NAb) which neutralize the biological activity of the drug and non-neutralizing antibodies (non-NAb), which bind to the drug, may altering the pharmacokinetics and/or pharmacodynamics and thereby compromising its effectiveness. Both neutralizing and non-neutralizing antibodies may alter the pharmacokinetics of the product by enhancing clearance (and thereby shortening serum half-life) or, conversely, by prolonging serum half-life and product activity.

Analytical assays for detecting and quantifying ADA have clinical significance and serve as an important measure of drug response as well as choice of therapy regime. It is thus essential to have suitable analytical methods in place for detection and characterization of ADA, to ensure patient safety and treatment efficacy. However, current assays are often performed under conditions that does not resemble the human biology. Typically, immunogenicity assessments rely on a relative signal readout using cell-based assays or surface-based ligand binding assays such as enzyme-linked immunosorbent assay (ELISA), mesoscale discovery (MSD), and surface plasmon resonance (SPR), where one of the interactions partners (e.g. a drug molecule) is immobilized on a surface. Most assays cannot directly distinguish between the presence of non-NAb or NAb, hence requiring multiple assays and orthogonal techniques. In addition, many of the prior art methods are very cumbersome and/or time consuming.

The presence of the therapeutic drug molecule in the sample (i.e. drug tolerance) may also affect assay performance negatively. An ideal methodology would therefore provide an absolute measurement of immunogenicity under biorelevant conditions (e.g. in a biological matrix and in the presence of the drug molecule), including assessment of ADA type (i.e., non-NAb or NAb).

WO 2021/046316 describes an immunoassay for detection of anti-drug antibodies (ADAs), such as anti-CI-Inhibitor antibodies (CI INH-ADA) in a test sample. The immunoassay comprises the steps of (i) acidic dissociation of the anti-drug antibodies from the drug within a provided test sample; (ii) neutralization of the test sample containing the dissociated drug-ADA complexes; (iii) incubation of the sample with excess binding affinity labeled drug; (iv) capture of the resulting ADA-binding affinity labeled drug complexes on an affinity binding substrate surface; (v) addition of tagged anti-human antibodies; and (vi) quantification of captured affinity-labeled drug-ADA complexes. POULSEN, N. N. et al. "Flow-induced dispersion analysis for probing anti-dsDNA antibody binding heterogeneity in systemic lupus erythematosus patients: Toward a new approach for diagnosis and patient stratification." ANALYTICAL CHEMISTRY, 2016, 88.18: 9056-9061 describes a method for detection of immune responses by detecting of autoantibodies against a fluorescently labeled double-stranded DNA (dsDNA) using flow-induced dispersion analysis.

A reference standard curve was provided by using a fixed concentration of the fluorescently labeled dsDNA and a model antibody against the dsDNA in a number of different concentrations. Thereafter, autoantibodies against the labeled dsDNA in six plasma samples from Lupus patients were determined based on the standard curve.

PEDERSEN, M. E., et al. "Size-based characterization of adalimumab and TNF-$\alpha$ interactions using flow induced dispersion analysis: assessment of avidity-stabilized multiple bound species." SCIENTIFIC REPORTS, 2021, 11.1: 1-10; describes the use of flow induced dispersion analysis (FIDA) for in-solution characterization of TNF-$\alpha$ and adalimumab interactions in pre-incubated buffer samples and the concentration of adalimumab in samples were determined based on the hydrodynamic radius of the labeled TNF-$\alpha$. Initially, the hydrodynamic radius (size) of the labeled TNF-$\alpha$ is measured in the absence of adalimumab, thus the size of unbound TNF-$\alpha$ is measured confirming the structural integrity of the molecule. As the concentration of adalimumab is increased, the apparent size of TNF-$\alpha$ increases due to a higher degree of binding.

US 2013/0344621 describes assay methods for the determination of one or more anti-drug antibody (ADA) isotypes in a sample. The method involves labeling the drug (fluorescence labeling preferred), incubating the fluorescently labeled drug with the sample (patient plasma or serum sample) and separating the fluorescently labeled drug and the complexes it has formed with anti drug antibodies according to size using chromatography. This method is rather cumbersome and time requiring.

WO 98/39656 describes a method for detecting the presence of an immunologically reactive molecule in a sample, comprising of placing the sample into contact with a standard solution of one or more immunologically reactive reference molecules in an incubation mixture in order to enable the formation of immune complexes between the immunologically reactive reference molecule and the immunologically reactive molecule for detecting, and determining whether immune complexes have been formed by comparing one or more of the physical parameters of molecular weight, charge and form of the components of the incubation mixture with the same physical parameters of the components of the standard solution, wherein determining whether immune complexes have been formed is brought about by column chromatographic separation of the components of the incubation mixture, column chromatographic separation of the components of the standard solution in the same manner as in the preceding separation and comparison of the elution patterns of both separations, wherein a change in the elution speed of the immunologically reactive reference molecule in the incubation mixture relative to the elution speed of the same immunologically reactive reference molecule in the standard solution indicates the formation of an immune complex.

DISCLOSURE OF INVENTION

An objective of the present invention is to provide a reliable and relatively fast method for determining a response characteristic of a drug comprising a chemical substance and especially to determining a response characteristic indicative of the presence of ADA in a sample.

In an embodiment, it is an object to provide a reliable and relatively fast method for determining an in vivo immunogenic response to a chemical substance.

In an embodiment, it is an object to provide a reliable and relatively fast method for determining an in vitro immunogenic response to a chemical substance. In an embodiment, it is an object to provide an immunology screening method.

In an embodiment, it is an object to provide a reliable and relatively fast method for determining a response characteristic of a drug comprising a chemical substance, wherein the response characteristic is indicative of the presence and type of ADA in a sample.

In an embodiment, it is an object to provide a reliable and relatively fast method for determining a response characteristic of a drug comprising a chemical substance, wherein the response characteristic is indicative of the amount of ADA in a sample.

In an embodiment, it is an object to provide a reliable and relatively fast method for determining a response characteristic of a drug comprising a chemical substance, wherein the response characteristic is indicative for the individual susceptibility of and/or immunogenic response to the drug.

In an embodiment, it is an objective to provide a reliable and relatively fast method for determining a response characteristic of a drug comprising a chemical substance, wherein the response characteristic is indicative for maintaining or adjusting the drug administration profile and/or for terminating the treatment with the drug.

In an embodiment it is an objective to provide a reliably and fast method for determining response characteristic of a substance in an animal, wherein the response characteristic is indicative of adverse effects related to the substance.

These and other objects have been solved by the inventions or embodiments thereof as defined in the claims and as described herein below.

It has been found that the inventions or embodiments thereof have a number of additional advantages, which will be clear to the skilled person from the following description.

The phrase "molecular interaction" means any non-covalent interactions between molecules as well as within one or more molecules.

The term "chemical substance" is herein used to mean any chemical substance at least partly dissolved or dissolvable in the biological liquid sample. In practice, the chemical substance may be any chemical substance suspected for being capable of triggering an immunogenic reaction. The chemical substance is conveniently a molecule or a complex, such as an antigen.

The term "drug" is used herein to mean an active agent, such as an active agent of a medicine or suitable for a medicine.

The term "target" is herein used to mean a target for the chemical substance unless otherwise specified.

The term "binding partner" is herein used to mean any molecule or group of molecules, capable of non-covalent interacting with the chemical substance.

The binding partner is conveniently identical (except for the marker) to the target for the chemical substance, a target analog and/or a molecule or complex which has binding site(s) for the chemical substance identical to or corresponding to the target. The binding partner may for example be a fragment of a target molecule The term "optical marker" is herein used to mean any intrinsic or extrinsic marker capable of being detected by an optical reader arrangement. In an embodiment, the marker comprises an element, group of elements, moieties and/or any combination comprising one or more of these, where the marker is capable of being detected by a reader arrangement directly and/or after being influenced from an external and/or internal source.

The term "reader arrangement" means any detector or detector system capable of detection a signal, such as an optical signal.

The term "buffer" means an aqueous solution, which is resistant to changes in pH value in the context where the buffer is used. The buffer advantageously comprises an aqueous solution of either a weak acid and its salt or a weak base and its salt.

Unless otherwise specified the pH value of a buffer system is determined at 20° C. The most stable pH value of a buffer system is the value where the buffer capacity is at maximum, i.e. where pH=pKa value The terms "test" and "assay" are used interchangeable.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

Reference made to "some embodiments" or "an embodiment" means that a particular feature(s), structure(s), or characteristic(s) described in connection with such embodiment(s) is included in at least one embodiment of the subject matter disclosed. Thus, the appearance of the phrases "in some embodiments" or "in an embodiment" in various places throughout the specification is not necessarily referring to the same embodiment(s). Further, the skilled person will understand that particular features, structures, or characteristics may be combined in any suitable manner within the scope of the invention as defined by the claims.

The term "substantially" should herein be taken to mean that ordinary product variances and tolerances are comprised.

Throughout the description or claims, the singular encompasses the plural unless otherwise specified or required by the context.

All features of the invention and embodiments of the invention as described herein, including ranges and preferred ranges, may be combined in various ways within the scope of the invention, unless there are specific reasons not to combine such features.

It has been found that the method of the invention provides a relatively fast and effective tool for determining an immunogenic response to a chemical substance, where the immunogenic response may be an in vitro immunogenic response or in vivo immunogenic response. The method may for example be applied as a screening method for screening drug candidates, as a pre-test method for estimating an individual's potential immunogenic response to a drug candidate, a control method for determine immunogenic response of an individual. Other beneficial applications of the method defined in the claims will be clear to a skilled person based on the disclosure provided herein.

In addition the method does not require any separation of complexes comprising the chemical substances and/or the binding partner. Specifically it was found that some anti-drug antibodies are only weakly bound to the drug. Thus, using separation e.g. chromatography size exclusion would not be able to detect weakly bound anti-drug antibodies as they will dissociate from the drug during the separation. The solution provided by the present invention is also suitable for determining anti-drug antibodies that are only weakly bound to the drug. The method of determining an immunogenic response characteristic of a chemical substance comprises obtaining a biological liquid sample comprising the chemical substance,
 providing at least one prepared sample from at least a portion of the biological liquid sample,
 for each prepared sample, subjecting at least a test portion of the prepared sample to a flow involving that the test portion of the prepared sample is in contact with a binding partner for the chemical substance, wherein the binding partner comprises an optical marker,
 performing at least one read out of the optical marker and based thereon, determining a characteristic flow parameter of the marked binding partner in contact with the prepared sample
 comparing the determined characteristic flow parameter with a respective reference value and determining the immunogenic response characteristic of the chemical substance.

The biological liquid sample may be a sample from an individual or it may be a sample from a mixture of individual, for example a biological liquid sample from a standard cell culture. The latter may specifically be suitable where the method comprises a screening method.

In an embodiment, the biological liquid sample is a sample from an individual, preferably from a mammal. Advantageously, the biological liquid sample is liquid sample obtained from a human; a farm animal, such as a goat, cattle, a llama, a pig a sheep or an alpaca; a rodent, such as a mouse or a rat; a Lagomorpha, such as a rabbit and/or a pet, such as a horse, a dog or a cat.

Since an immunogenic reaction may be triggered in any liquids of an individual, the biological liquid sample may in principle be any biological liquid from living mammals or cell cultures therefrom.

Advantageously, the biological liquid sample is selected from extracellular fluid, intracellular fluid, blood, urine, semen (seminal fluid), vaginal secretions, cerebrospinal fluid (CSF), synovial fluid, pleural fluid (pleural lavage), pericardial fluid, peritoneal fluid, amniotic fluid, saliva, nasal fluid, mucus, optic fluid, gastric fluid, breast milk, cell culture fluid or any combinations thereof.

It has been found to be very beneficial to apply a marked (also often referred to as labelled) binding partner for the chemical substance, the patient will by fully unaffected of any labelling—i.e. neither the chemical substance or any optional antibodies resulting of the immunogenic response requires to be labelled.

Advantageously, the chemical substance is at least partially dissolvable in the biological liquid sample. Preferably, the chemical substance comprises a chemically active entity, a chemically active molecule or a chemically active complex.

The chemical substance may for example be a chemically active entity, such as a pharmaceutical/biologically active ingredient of or for a medicine.

Examples of chemical substances comprises proteins, peptides, biologically active polymeric agent, biologically active inorganic agent, biologically active metallic agent or any combination thereof.

In an embodiment, the chemical substance comprises a biopharmaceutical, preferably selected from cytokines, antibodies, enzymes, hormones, immune modulators, vaccine agents.

In an embodiment, the biopharmaceutical comprises a monoclonal antibody.

As explained above, it has been found that for many biopharmaceutical there may be a substantially risk of development of an undesired immunogenic response and therefore the method presented herein is specifically preferred where the chemical substance comprises biopharmaceutical.

In an embodiment, the chemical substance is an active agent for treatment of at least one of cancers, cardiovascular diseases, metabolic diseases or neurodegenerative diseases. The medicine applied for treatment of such disease are often administered to an individual over a long period such as for several, weeks, months or even years, and it has been found that the immunogenic response of an individual treated with a medicine comprising a chemical substance may often change over time. Often the individual needs to be regularly tested for immunogenic response using expensive and often time demanding methods. The method of the invention provides a highly beneficial method for such applications.

A highly beneficial property of the present method is that the method may be applied not only to determine the immunogenic response (i.e. non-immunogenic response or immunogenic response), but the method may also be applied for determine a level of Anti-Drug-Antibody (ADA) generation and what it especially beneficial is that the method simultaneously may be applied for determine which type of ADA are generated, namely neutralizing antibodies (NAb) or of non-neutralizing antibodies (non-NAb).

Without being bound by the theory, it is believed that where the chemical substance is acting in a normal and desired mode i.e. where the response is a non-immunogenic response, the chemical substance will be reacting with the target in the form of the marked binding partner according to normal reaction kinetic and with a $K_D$ value (equilibrium dissociation constant) which may be known or unknown. In case of neutralizing antibodies (NAb) a significant part of the chemical substance, depending on the level of neutralizing antibodies (NAb), will be bound to the neutralizing antibodies (NAb) and blocking for reaction with the marked binding partner, which mean that a less chemical substance is free to be reacting with the marked binding partner, thus leaving an increased amount of marked binding partner un-bound in the sample. In case of non-neutralizing antibodies (non-NAb), a significant part of the chemical substance, depending on the level of non-neutralizing antibodies (non-NAb), will be bound to the of non-neutralizing antibodies (non-NAb), but without blocking for reaction with the marked binding partner, which mean that complexes of the chemical substance, the of non-neutralizing antibodies (non-NAb) and the marked binding partner will be present.

Thereby, by detecting the flow characteristic of the marked binding partner, the reaction kinetic and equilibrium binding may be determined and thereby the immunogenic response of the chemical substance may be determined.

The step of providing at least one prepared sample may advantageously comprise diluting the biological liquid sample to lower the concentration of the chemical substance. It has been found to be more accurate to detect the state of the chemical substance and thereby the potential immunogenic response and optional generation of ADA.

The step of providing at least one prepared sample may comprise diluting the biological liquid sample to a selected concentration of the biological liquid sample or to a selected or estimated concentration of the chemical substance.

The dilution degree may, as mentioned be set in relation to the concentration of the biological liquid sample or to a selected or estimated concentration of the chemical substance. It is preferred that the reference value is correlated to a corresponding concentration of the biological liquid sample or the selected or estimated concentration of the chemical substance.

Advantageously, the step of providing at least one prepared sample comprises adding a buffer system to the portion of the biological liquid sample, preferably to provide a desired concentration of biological liquid sample or selected/estimated concentration of the chemical substance. Depending on the desired accuracy of the determination, two or more prepared samples having different concentrations of biological liquid sample or different concentrations of selected/estimated concentration of the chemical substance.

In an embodiment, the provision of at least one prepared sample from the biological liquid sample comprises providing a plurality of prepared samples from the body fluid sample. Advantageously, wherein the plurality of prepared sample comprises at least 2, such as at least 3, such as 4 to 100 prepared samples having different selected biological liquid sample concentration.

Where the plurality of prepared sample comprises samples having different selected biological liquid sample concentration, these samples will have different concentration of the chemical substance (except where the chemical substance is not present)

The phrase "concentrations of biological liquid sample/concentration of chemical substance" is in the following applied to mean "concentrations of biological liquid sample and/or concentration of the chemical substance, which may advantageously be known or estimated.

It has been found that the detection of immunogenic response is more accurate at some concentrations of biological liquid sample or selected/estimated concentration of the chemical substance than at other concentration thereof.

It may therefore be beneficial to provide prepared samples having different concentrations of biological liquid sample/concentration of chemical substance, to identify an optimal concentration of biological liquid sample/concentration of chemical substance reaction pattern for performing the determination. Where the determination comprises determination at several different concentrations of biological liquid sample/concentration of chemical substance a more detailed reaction pattern may be observed. In addition, it may be possibly to reveal an immunogenic response at a very early stage.

Where the method comprises providing two or more prepared samples having different concentrations of biological liquid sample/concentration of chemical substance the respective reference values for the prepared samples may advantageously be provided in form of a reference binding curve, such as a binding curve of the characteristic flow parameter e.g. hydrodynamic radius parameter or dispersion parameter for the chemical substance and marked binding partner as a function of concentration of the chemical substance.

The determined characteristic flow parameter of the respective prepared samples may then be provided as a determined binding curve and the goodness of the determined binding curve to the reference binding curve may be determined and may provide the determined immunogenic response characteristic of the chemical substance.

The buffer systems are well known to the skilled person and may conveniently include buffer systems that have a buffer pH value of from about 4 to about 8. Preferably the buffer system is selected from a phosphate buffer system, a PBS (Phosphate buffered saline) buffer system, a tris (tris (hydroxymethyl)aminomethane) buffer system and a hepes ((4-(2-hydroxyethyl)-1-piperazineethanesulfonic acid) buffer system.

As it will be explained further below the marked binding partner may be added to the prepared sample or the marked binding partner may be added to a support liquid, which in the flow step is brought in contact with the test sample portion of the prepared sample.

For increasing the accuracy, two or more identical test samples are provided from a prepared sample for performing determinations in duplicate, triplicate or further replication.

The step of subjecting the prepared sample to a flow preferably comprises subjecting the sample to a laminar flow. The laminar flow is advantageously provided for a sufficient time to performing the at least one read out of the optical marker, preferably the read out of the optical marker is performed after at least 5 seconds, such as at least 10 seconds, such as at least 30 seconds, such as at least 1 minute, such as at least 5 minutes where the prepared sample has been in laminar flow.

The characteristic flow parameter may in principle be any flow parameter that are dependent on the molecular size or average molecular size of the molecule or complex containing the marked binding partner, such as any mass transport parameters.

Very accurate determination may specifically be obtained where the characteristic flow parameter comprises a dispersion parameter, a diffusion parameter e.g. diffusion coefficient, a hydrodynamic radius parameter or any derivatives thereof. Preferably, the characteristic flow parameter comprises at least one of a weighted average hydrodynamic radius of the marked binding partner and complexes comprising the marked binding partner and a weighted average dispersion of the marked binding partner and complexes comprising the marked binding partner or any derivatives thereof.

In general the method may be carried out in different modes comprising a) providing the marked binding partner to be in the test portion of the prepared sample prior to introducing the test portion to the flow, b) adding the marked binding partner to the test portion after the test portion has been introduced to a channel for the flow, optionally where the flow has been initiated and c) bringing the marked binding partner e.g. in a support liquid, in contact with the test portion of the prepared sample while the test portion is in flow. As mentioned the flow is advantageous a laminar flow. It should be noted that the three modes may be combined in any suitable way.

The test portion may be the prepared sample or a part of the prepared sample. For increasing accuracy, it is desired to provide several test portions from the prepared sample for performing the determinations 2, 3, 4 or more times and apply the average result from the determinations.

In an embodiment, two or more test portions of a prepared sample are tested according to the third mode where the concentration of the marked binding partner differs in the test of the respective test portions.

Advantageously, the method comprises adding the marked binding partner to the prepared sample prior to subjecting the a prepared sample or a test portion thereof to the flow or the method comprises bringing the marked binding partner in contact with the prepared sample in a flow channel.

In an embodiment, the marked binding partner is added to the prepared sample in a selected concentration, preferably the marked binding partner is added to the prepared sample together with addition of the buffer.

The marked binding partner may advantageously be added in surplus.

In an embodiment, the marked binding partner is added in an amount to reach a concentration in the prepared sample, which is at least twice, such as at least three times the estimated concentration of naturally present target components.

In an embodiment, the provision of at least one prepared sample from the biological liquid sample comprises providing a plurality of prepared samples from the body fluid sample, wherein the selected molar concentration of the marked binding partner for each of a plurality of the prepared samples are identical or up 10 mol % in variation, preferably the selected molar concentration of the marked binding partner for all of the prepared samples are identical or up 10 mol % in variation, optionally the selected molar concentration of the marked binding partner for 2 or more of the prepared samples differs from each other.

In an embodiment, the marked binding partner is added in an amount to provide that the molar concentration thereof is at least 1% of an estimated molar concentration of the chemical substance, preferably the marked binding partner is added in an amount to provide that the molar concentration thereof is at least 5%, such as at least 10%, such as at least 25%, such as 100% or more of an estimated molar concentration of the chemical substance.

To ensure that determination is performed with amounts of chemical substance, which provides a high signal to noise, it is desired to perform the test on test portions having different concentration of the chemical substance. Thus if the chemical substance is very high, the marked binding partner may bind to chemical substance even though some chemical substance is neutralized by the non-neutralizing antibodies (non-NAb), which thereby may make it difficult to detect potential of non-neutralizing antibodies (non-NAb). On the other hand, if the concentration of the chemical substance is too low, it may be difficult to detect a clear signal at all.

In a preferred embodiment, the provision of at least one prepared sample from the biological liquid sample comprises providing a plurality of prepared samples from the body fluid sample by adding a buffer system, wherein the respective prepared sample are provided to have different concentration of the biological liquid sample, preferably plurality of prepared samples are provided by preparing a dilution series.

In an embodiment, the determination of the characteristic flow parameter is performed by a method comprising subjecting the test portion of the at least one prepared sample and at least one support liquid to a laminar flow in a common channel, wherein the test portion is in interfacial contact with the support liquid, detecting a concentration profile of the optical marker and determine the characteristic flow parameter.

The support liquid may advantageously be or comprises a buffer system. The buffer system may e.g. be as described above. Advantageously, the buffer system of the support liquid has same pH value and is preferably identical to an optional buffer system of the prepared sample.

In an embodiment the support liquid comprises additional active components selected from an additional binding partner (such as a target) for the chemical substance and/or a marked chemical substance corresponding to (Biosimilars) or identical to the chemical substance, wherein the additional active component is non-marked or preferably marked with a different marker than the marker of the marked binding partner. Thereby additional information about the immunogenic response may be obtained.

In an embodiment, the test portion of the at least one prepared sample and at least one support liquid is fed into the common channel in respective portions one after the other along the length of the common channel, where after the portions are subjected to the laminar flow. Additional "plugs" of test portion and support liquid may be fed to the channel in an alternating fashion. Each "plug" of test portion may be equal or different—e.g. different test portions as described above. Thereby, a plurality of tests of test portions may be provided very fast.

As mentioned above the binding partner may be present in any one of the test portions and the support liquid.

In an embodiment, the method comprises adding the marked binding partner to the prepared sample prior to feeding the sample into the common channel.

In an embodiment, the method comprises adding the marked binding partner to the support liquid prior to feeding the support liquid into the common channel.

In an embodiment, the test portion of the at least one prepared sample is fed into the common channel and mixed with the support liquid in the channel, wherein the support liquid comprises the marked binding partner.

In an embodiment, the method comprises feeding a first portion of the support liquid into the common channel, feeding the test portion into the common channel to be in interfacial contact with the first portion of the support liquid and feeding a second portion of the support liquid into the common channel to be in interfacial contact with the test portion and subjection the portions to the laminar flow.

In an embodiment, the test portion and the support liquid is provided to form adjacent layers of a laminar flow. This may for example be provided by feeding the test portion and the support liquid into the common channel to be in laminar flow adjacent to and in contact with each other.

In an embodiment, the determination of the characteristic flow parameter is performed using a multifurcated channel arrangement comprising the common channel and two or more input channel portions that are merged at a downstream located merging location to form the common channel, wherein the test portion and the support liquid are subjected to the laminar flow by feeding the test portion to one of the input channel portion and the support liquid to one or more other of the input channel portion and providing the laminar flow where the test portion is in interfacial contact with the support liquid in the common channel downstream to the merging location. This method may be very effective for determining the characteristic flow parameter in the form of a dispersion parameter.

The optically readable marker may be any type of optical marker, such as the markers known in the art. In an embodiment, the optically readable marker is a light absorbing marker and/or a fluorescent marker, and/or chemiluminescence marker preferably operating in the UV/Vis wavelength range preferably from about 190 nm to about 700 nm.

The reading out of the concentration profile may in principle be performed by any method such as known methods for performing optical readings. The reading out may e.g. be performed by using a reader arrangement comprising an electronic detector such as a photomultiplier tube (PMT), charged coupled detector (CCD photo resistor and/or photodiodes e.g. an avalanche photo diode.

In an embodiment, the reading out of the concentration profile of the marker is performed at a detection location of the channel while the test portion and the support liquid is in laminar flow in the channel at the detection location. Thereby very accurate readings may be obtained in a fast and effective way.

To provide a significant signal it is desired that the portion and the support liquid is in laminar flow at the time of reading out and preferably for at least a time prior to the reading out.

Advantageously, the test portion and the support liquid is in laminar flow for at least 5 seconds, such as for at least 10 seconds, such as for at least 100 seconds, such as for at least 200 seconds, such as for 0.5-25 minutes, such as for 1-10 minutes prior to performing of the detection of the concentration profile of the marker.

The common channel may be any kind of channel suitable for subjecting the test portions to the flow, preferably suitable for providing the test portions and the support liquid to the laminar flow.

The common channel may advantageously be a microfluidic channel, e.g. forming part of a microfluidic device.

The common channel may advantageously have a maximal inner dimension of about 1 mm or less, such as of about 0.5 mm or less, such as of about 0.1 mm or less, such as of about 75 μm or less, preferably the channel has a circular or oval cross sectional shape.

In an embodiment, the channel has equal inner dimension(s) along at least a length section, such as along its entire length.

In an embodiment, the channel has a tapered channel length section, such as a narrowing channel length section and/or a widening channel length section.

In an embodiment, the liquid portions are fed to the channel at same or different pressure such as one or more pressures of at least 50 mbar, preferably to fill each of the respective liquid portions into the channel during a period of up to about 60 minutes or more, such as from about 5 seconds to about 5 minutes.

In an embodiment, the flow velocity of from about 0.1 cm/min to about 50 cm/sec, such as from about 1 cm/min to about 25 cm/sec, such as from about 5 cm/min to about 10 cm/sec, such as from about 10 cm/min to about 5 cm/sec.

In an embodiment, an apparatus as described in copending application PCT/DK2021/050079, with the difference that the computer system of the assessment system is programmed to perform the method described above. In addition, the apparatus is not set to perform a condition jump.

Advantageously, the temperature is held constant, preferably at a temperature between 5 and 37° ° C., such as between 15 and 30° ° C.

It has been found that the prepared sample need not be subjected to an incubation time prior to being subjected to the laminar flow, However, where the binding partner is added to the prepared sample prior to subjecting the test portion thereof to the flow, it may be beneficial to subject the prepared sample to an incubation, to thereby reduce the requires flow time.

In an embodiment, each prepared sample is subjected to an incubation time prior to being subjected to the laminar flow, wherein the incubation time is at least 5 seconds, such as at least 10 seconds, such as 0.5-10 minutes, such as 1-5 minutes prior to providing the laminar flow.

In an embodiment, one or more of the prepared samples are subjected to a longer incubation time, such as 1 hour or more e.g. an overnight incubation, such as 16-24 hours.

The respective reference values advantageously comprises values representing a non-immunogenic response, preferable with no or insignificant level of neutralizing antibodies (NAb) and non-neutralizing antibodies (non-NAb) for the chemical substance. Alternatively the reference value(s) could be selected as value(s) representing an immunogenic response with significant level of non-neutralizing antibodies (non-NAb) or the reference value(s) could be selected as value(s) representing an immunogenic response with significant level of neutralizing antibodies (NAb).

In an embodiment, the respective reference values are provided in the form of a reference binding curve, such as a binding curve of the characteristic flow parameter e.g. hydrodynamic radius parameter or dispersion parameter for the chemical substance and marked binding partner as a function of concentration of the chemical substance, preferably no or insignificant level of neutralizing antibodies (NAb) and non-neutralizing antibodies (non-NAb) for the chemical substance.

The reference values may be provided from previous determinations, by calculation or a combination thereof.

In an embodiment, the respective reference values comprises at least one reference value obtained from previous determination performed on one or more biological liquid samples from individuals with a non-immunogenic response. Preferably, the previous determination of the reference values are obtained for and correlated to corresponding concentrations of biological liquid sample and/or of chemical substance.

It has been found to be very beneficial that at least one of the reference values represents a normal response determined on a biological liquid with no anti-drug antibodies or only an insignificant or acceptable level of neutralizing antibodies (NAb) and/or non-neutralizing antibodies (non-NAb) for the chemical substance.

In particular it has been found that the use of one or more reference values representing a normal response provides an increased accuracy in determining the immunogenic response characteristic and in particular determining if the immunogenic response is positive (no adverse effects) or negative (risk of adverse effect(s)). Especially, the risk of false positive may be reduced.

In an embodiment, where the determined characteristic flow parameter is a numeral determination, using of one or more reference values representing a normal response provides an efficient and accurate basis for classifying the immunogenic response characteristic e.g. into level of immunogenic response and/or character of immunogenic response, such as non-immunogenic response, immunogenic response comprising formation of neutralizing antibodies (NAb) and/or an immunogenic response comprising formation of non-neutralizing antibodies (non-NAb).

In an embodiment, the respective reference values comprises at least one calculated reference value, preferably based on one or more of molecular size of the chemical substance, molecular size of the marked binding partner, $K_D$ value (equilibrium dissociation constant) for the chemical substance and marked binding partner, dispersion of the marked binding partner and/or a complex comprising the marked binding partner and the chemical substance and/or any derivatives thereof, the viscosity of the prepared sample and/or the support liquid. Molecular size can for example be determined as hydrodynamic radius or from molecular diffusivity.

In an embodiment, the respective reference values comprises a reference binding curve and/or reference values taken therefrom. The reference binding curve may for example be based on the equilibrium dissociation constant (Kd), and the hydrodynamic radius parameter or dispersion parameter of respectively the marked binding partner and the marked binding partner-chemical substance complex.

Lists of reference values correlated to sets of marked binding partner, molecule sizes and concentration of chemical substances and/or KD values may be provided for general application. For some sets of marked binding partner, molecule sizes and concentration of chemical substances and/or KD values listed reference value may be found in the RCSB protein data bank.

To provide a fast grating of determined characteristic flow parameter it may be desired to provide a factor classification for a given chemical substance/marked binding partner pair. Such a grating system may be very beneficial for a fast immunogenic response determination and in particular beneficial where the method comprises a screening method.

In an embodiment, the respective reference values comprises at least one reference value provided by a response factor classification associated to a selected concentration of biological liquid sample or a selected concentration of chemical substance. Preferably, the response factor classification comprises an indication of a factor range indicating non-immunogenic response, a factor range indicating an immunogenic response comprising formation of neutralizing antibodies (NAb) and/or a factor range indicating an immunogenic response comprising formation of non-neutralizing antibodies (non-NAb).

Advantageously, one or more, such as all of the respective reference values provided by a response factor classification associated to a selected concentration of biological liquid sample or a selected concentration of chemical substance is/are reference values representing respective responses in the determined on respectively a) a biological liquid with no anti-drug antibodies or only an insignificant or acceptable level of neutralizing antibodies (NAb) and/or non-neutralizing antibodies (non-NAb) for the chemical substance,
b) a biological liquid with a selected level of neutralizing antibodies (NAb) for the chemical substance and
c) a biological liquid with a selected level of non-neutralizing antibodies (non-NAb) for the chemical substance.

In an embodiment, b) and/or c) may have two or more sub-levels with different selected levels.

In an embodiment, the method comprises in vitro test of a chemical substance in the form of a drug candidate (such as an active agent) for treatment of a medical condition involving a target molecule, wherein the method comprises, subjecting a cell culture comprising the target with the drug candidate according to a selected program and obtaining the biological liquid sample from the cell culture, preferably the method further comprises determining if the drug candidate is passing as a drug candidate e.g. for further analysis, for starting clinical tests, for approval for use etc.

The selected program may be any program, e.g. subjecting the cell culture to the selected concentration of the drug one time or several times over a period. In an embodiment, the selected program may correspond to an estimated administration plan, for example including dosage/time of dosage etc.

The screening method may comprise screening a plurality of drug candidates, e.g. in a high throughput fashion, for example to eliminate drugs with high risk of generating undesired immunogenic response or to examine the immunogenic response in various conditions.

In an embodiment, the provision of the prepared sample of each drug candidate comprises adding buffer system to a selected concentration of the biological liquid sample or of the drug candidate and wherein the step of comparing the determined characteristic flow parameter with a respective reference value and determining the immunogenic response characteristic of the chemical substance for the drug candidate(s) comprises comparing the determined characteristic flow parameter with response factor classification associated to the selected concentration of the biological liquid sample or of the drug candidate and classifying the determined immunogenic response as a non-immunogenic response, an immunogenic response comprising formation of neutralizing antibodies (NAb) or an immunogenic response comprising formation of non-neutralizing antibodies (non-NAb).

For a very rough and fast sorting, it may be sufficient performing the test for one single concentration of biological liquid sample/concentration of chemical substance. For improved accuracy, it may be desired to perform the test for several concentrations of biological liquid sample/concentration of chemical substance.

In an embodiment, the respective determinations is performed for at least two different selected concentrations of the biological liquid sample or of the drug candidates.

The drug candidate may beneficially be a drug candidate for development of a drug for treatment of a disease, such as for treatment of at least one of cancers, cardiovascular diseases, metabolic diseases or neurodegenerative diseases.

Advantageously, the drug candidate is a drug candidate for treatment of a condition of an individual and the sample, such as a biological liquid and/or a cell culture is a sample of the individual.

In an embodiment, the sample is of an individual under pre-examination for treatment with the drug candidate and wherein the determined response characteristic is indicative for the individual's risk of generating undesired immunogenic reactions triggered by the drug candidate.

The method may preferably be applied for determining e.g. monitoring an individual in respect of immunogenic response or change of immunogenic response where the individual is treated with the chemical substance.

In a preferred embodiment, the biological liquid sample is a sample obtained from an individual subjected to treatment with the chemical substance according to a drug administration program and wherein the determined response characteristic is indicative for a response of the treatment.

Advantageously, the determined response characteristic is indicative for, if the response of the treatment involves formation of Anti-Drug-Antibody (ADA), and preferably for the level of ADA generation and/or if the treatment involves formation of neutralizing antibodies (NAb) or of non-neutralizing antibodies (non-NAb).

In an embodiment, the method comprises classifying the determined immunogenic response as a non-immunogenic response, an immunogenic response comprising formation of neutralizing antibodies (NAb) or an immunogenic response comprising formation of non-neutralizing antibodies (non-NAb).

In an embodiment, the determined response characteristic may be indicative for maintaining or adjusting the drug administration program. Thus, based on the determined immunogenic response characteristic the physician may decide that the treatment of the individual may be continued according to a current drug administration program or the physician may decide to continue the treatment with an adjusted drug administration program, such as a reduction in dosage or frequency of administration or in case of no indication of undesired immunogenic response, the physician may decide to increase the dosage or frequency of administration.

In an embodiment, the determined response characteristic is indicative for terminating the treatment with the drug and based on this the physician may decide to terminate the treatment or switch to another drug.

All features of the invention(s) and embodiments thereof including ranges and preferred ranges can be combined in various ways within the scope of the invention, unless there are specific reasons not to combine such features.

BRIEF DESCRIPTION OF THE EXAMPLES AND DRAWING

The invention is being illustrated further below in connection with examples and embodiments and with reference to the figures. The figures are schematic and may not be drawn to scale. The examples and embodiments are merely given to illustrate the invention and should not be interpreted to limit the scope of the invention.

FIG. 3 illustrates the injection process used in example 1a.

FIG. 6 shows the resulting determinations of characteristic flow parameters for 40 serum samples tested in example 1a.

FIG. 7 shows the hydrodynamic radius of TNF-α-AF488 (100 nM) alone+complexes thereof as a function of serum concentration as determined in example 1a.

FIG. 8 shows the 30 tested serum samples classified as NAb positive, normal responders, and non-NAb positive can be identified.

Figure 1:
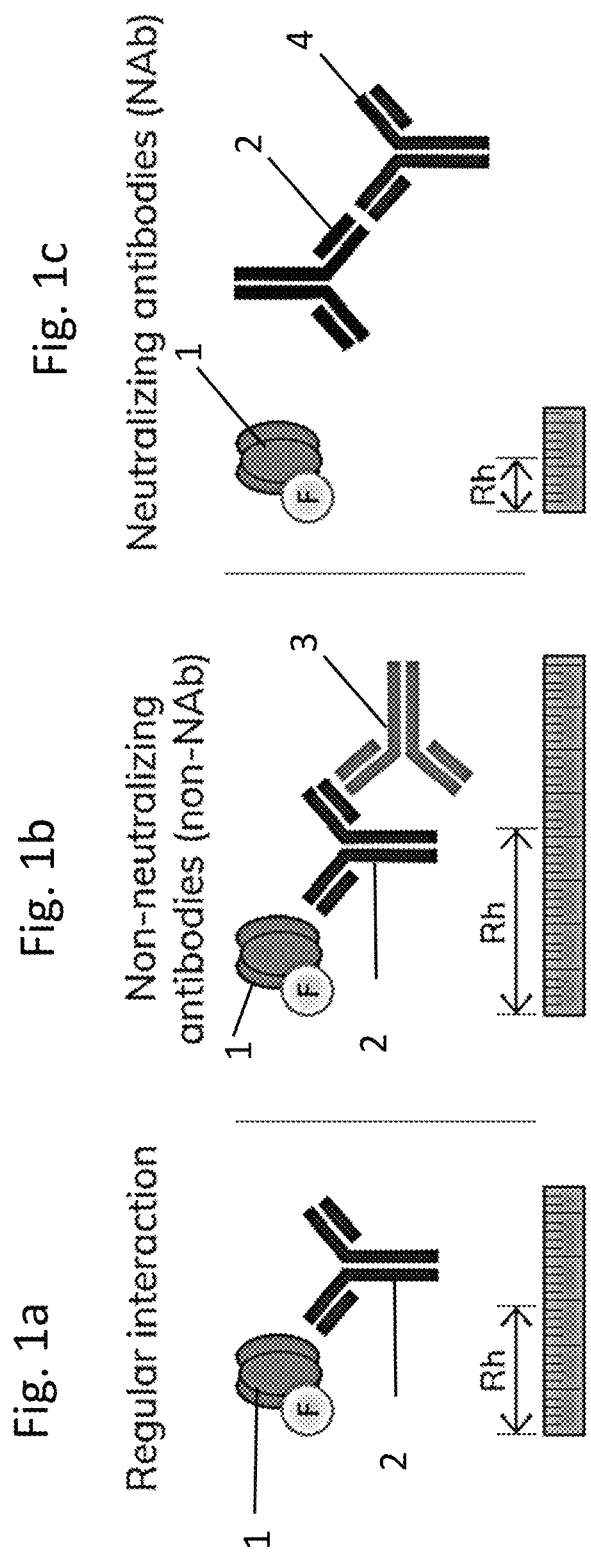
FIGS. 1a, 1b and 1c are schematic illustrations showing ADA classification as function of apparent hydrodynamic radius (Rh) of TNF-α (indicator) and adalimumab (analyte).

FIG. 1a-1c illustrate the hydrodynamic radius (Rh) of the marked binding partner or the complex comprising the marked binding partner. The marked binding partner 1, in marked by the fluorescent marker F. In FIG. 1a, the marked binding partner is 1 bound to the chemical substance 2. This indicates a regular interaction. The Rh is indicated at the bottom of the FIG. 1a.

In FIG. 1b, the marked binding partner is 1 bound to the chemical substance 2. However the chemical substance 2 is already bound to a of non-neutralizing antibody (non-NAb) 3. This indicates an immunogenic reaction involving of non-neutralizing antibodies (non-NAb). The Rh is indicated at the bottom of the FIGS. 1b and 1t can be seen that it is larger than the Rh of the normal interaction.

In FIG. 1c, the marked binding partner is 1 is unbound bound. This is because the chemical substance 2 is bonded to and neutralized by a neutralizing antibody (NAb 4). This indicates an immunogenic reaction involving of neutralizing antibodies (NAb). The Rh is indicated at the bottom of the FIG. 1b is the RH of the marked binding partner and it can be seen that it is smaller than the Rh of the normal interaction.

Figure 2:
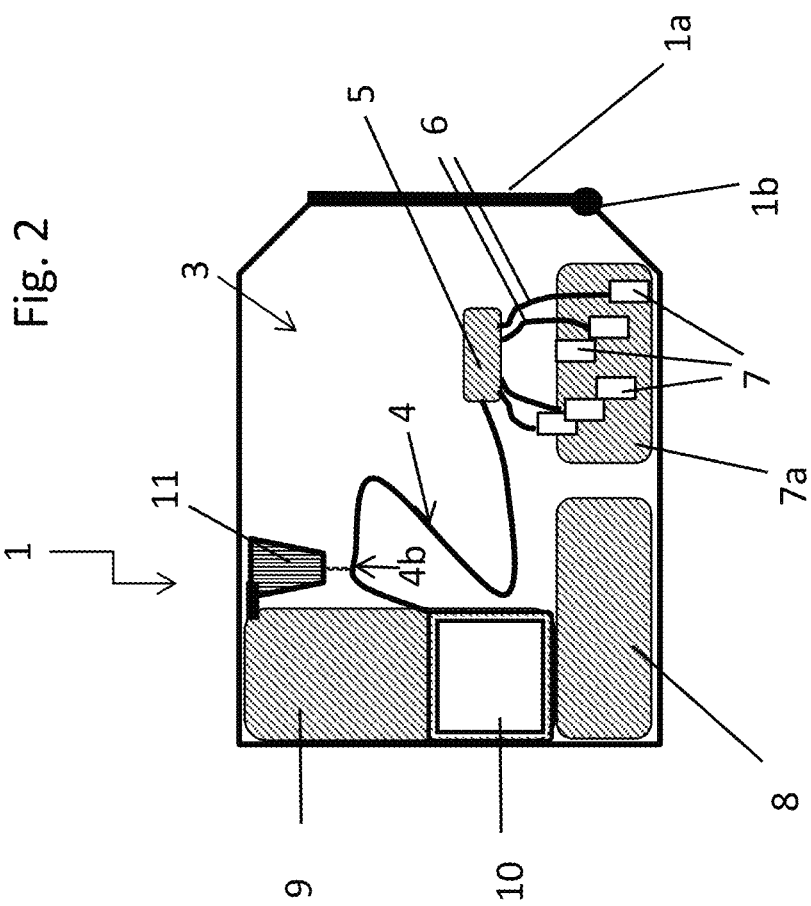
FIG. 2 illustrates an embodiment of an assessment system, which may be applied for performing the assessment of the characteristic flow parameter of an embodiment of the method of the invention.

The assessment system of FIG. 2 comprises an apparatus 11 having a compartment 31 comprising a microfluidic unit 4 forming a channel.

The compartment 13 comprises a plurality of mother sample containers 17 for containing respective prepared samples and buffer. The sample containers 17 are arranged in a support unit 17a. The support unit 17a advantageously comprises a temperature controller for temperature controlling of the liquids in the respective mother sample containers 17 to a selectable temperature. The compartment 13 comprises a withdrawing arrangement comprising a pump arrangement 15, connected to a plurality of withdrawing tubes 16. The respective tubes 16 may be manually inserted into desired mother sample. In an embodiment, the apparatus 11 comprises a robot arm adapted for inserting the tube(s) 16 into selected mother sample container(s).

In a variation of this embodiment the withdrawing arrangement comprising a single withdrawing tube which may be moved from one mother sample container to another for collecting the first liquid portion and the second liquid portion and optionally further liquid portion(s).

The apparatus 11 comprises a hinged 11b lid 11a into the compartment 13 for providing access.

In this embodiment, a microfluidic unit 14 in the form of tube with a narrow diameter is provided for ensuring a laminar flow of the test sample(s). The tube 14 is connected to the pump arrangement, such that the pump can pump withdrawn mother sample into the channel of the microfluidic unit 14 at a desired pressure difference.

The compartment 13 further comprises a computer 9 forming part of a computer system. The computer is adapted for controlling the elements of the apparatus 11. The computer 19 is connected to a reader arrangement 21 located for optically reading from a reading location 14b of the channel of the microfluidic unit 14.

The compartment 13 comprises temperature controller 18 for controlling the temperature in the compartment 13 to maintain a desired temperature.

A waste chamber 20 is located for collecting used liquid portions and optional cleaning fluid passed through the channel of the microfluidic unit 14.

In use, a first liquid portion and a second liquid portion are withdrawn from respective selected mother sample containers 17 using the tubes 16 and the pump arrangement 15 of the withdrawing arrangement.

The liquid portions are fed in succession into the channel of the microfluidic unit 14 to provide an interfacial contact between the first liquid portion and the second liquid portion. The liquid portions are thereafter pumped towards the reading arrangement 21.

EXAMPLES

Example 1a

In this example TNF-α is a drug target for a chemical substance in the form of a monoclonal antibody-based drug such as adalimumab. The mode of action of the antibody-based drug compounds is to bind and neutralize TNF-α in the patients.

The TNF-α is labeled using a fluorescence reporter such as Alexa Fluor 488, FITC, Atto-488, or similar.

Materials and Methods

Recombinant human TNF-α (cat. no. ab155699) was purchased from Abcam (Cambridge, United Kingdom). Alexa Fluor 488 (cat. no. A20181) labeling kits were purchased from Thermo Fisher (Waltham, MA, USA). Disodium hydrogen phosphate dihydrate, and sodium dihydrogen phosphate monohydrate were purchased from Merck (Darmstadt, Germany). Purified water (18.2 MΩ-cm, 25° C.) was obtained from an SG Ultraclear water purification system (SG Water, Barsbuttel, Germany). A 67 mM phosphate buffer (pH 7.4) was prepared, filtered (Q-max 0.45 μm nylon syringe filter from Frisenette (Knebel, Denmark)) and used as assay buffer. TNF-α was labelled with Alexa Fluor 488 using a commercial labeling kit.

FIDA (Flow Induced Dispersion Analysis) experiments were conducted on a FIDA 1 Platform instrument employing light-emitting-diode (LED) induced fluorescence detection with excitation wavelength: 480 nm and emission wavelength: >515 nm. The FIDA 1 Platform instrument is commercially available from Fida Biosystems ApS (Copenhagen, Denmark).

Standard capillaries with inner diameter 75 μm, outer diameter 375 μm, total length 100 cm, length to detection window 84 cm, from Fida Biosystems were used for all experiments. The capillaries were coated with high-sensitivity coating reagent (Obtainable from Fida Biosystems) prior to use.

Immunogenic response characteristic of the chemical substance adalimumab were determined for 40 patient. 5 of the patient, namely patient 1-5 were not treated with adalimumab, 5 patients, namely patient 6-10 were treated with another TNF inhibitor than adalimumab and the remaining 30 patient were treated with adalimumab. Adalimumab were administrated to the patients with the aim to achieve constant serum concentration of adalimumab. In practice, it may vary up to 50%.

From each serum sample a plurality of prepared samples, namely 8 prepared samples were provided by adding assay buffer 67 mM phosphate buffer (pH 7.4). The 8 prepared samples were provided as a dilution series with the concentration of serum in buffer in V/V %: 40, 20, 15, 10, 5, 1, 0.1 and 0.01.

The following stepwise procedure was applied for the FIDA determination (i.e. subjecting a test sample of the prepared sample to a flow in contact with the marked binding partner, TNF-α-AF488 (also referred to as indicator) and reading out) with an overall analysis time between 5-6 minutes per sample.

First, assay buffer (pH 7.4; 67 mM) was used for flushing and equilibrating the HS-coated capillary at 3500 mbar for 120 s. A first portion of the prepared sample was then filled into the capillary at 3500 mbar for 20-25 s followed by injection of a second portion of the prepared sample (the test portion) into which the indicator (TNF-α-AF488 in a concentration of 100 nM) had been mixed, at 50 mbar for 10 s. Lastly, the previously injected portions including the test portion were mobilized to the fluorescence detector with a third portion of the prepared sample at 400 mbar for 180-240 s.

Figure 3:
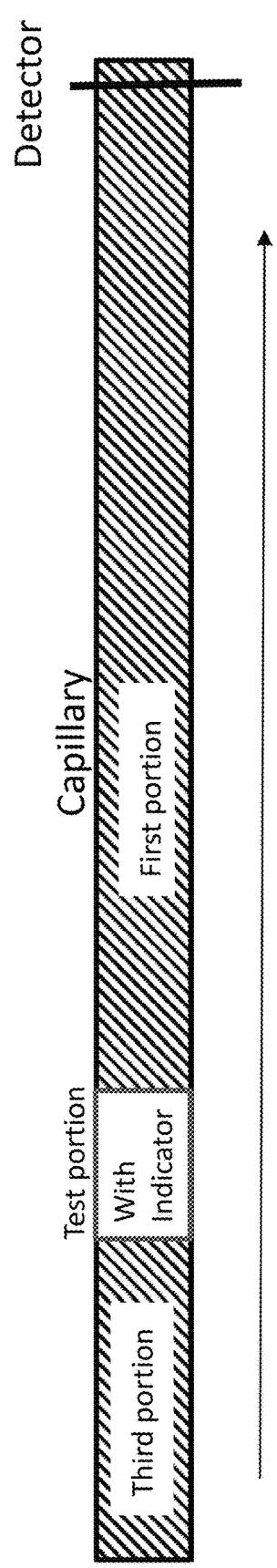

The injection process is illustrated in FIG. 3. The arrow indicates the flow direction In this example, the second portion of the prepared sample is the test portion and as mentioned, the test portion comprised TNF-α-AF488, which was premised with the second2 portion of prepared sample.

It should be noted that the first portion and third portion could have been replaced by serum or buffer with or without adalimumab.

Reference Values in the Form of a Binding Curve

The hydrodynamic diameter Rh of fluorescently labeled TNF-α is determined using a FIDA 1 Platform instrument in buffer as well as in plasma from healthy (non-treated) individuals. Data analysis is performed in the software accompanying the FIDA 1 Platform instrument. The result confirms a trimeric structure of TNF-α (Rh=3.2 nm). The fluorescently labeled TNF-α is titrated with adalimumab to determine a binding curve which was used as the reference binding curve.

The assays were performed in triplicate.

Results

The resulting determinations of characteristic flow parameters are shown in FIG. 6.

Reference values taken from the reference binding curve were applied as benchmark values. Based on the values from each patient it was determined if the drug response was a normal drug response, if non-neutralizing antibodies (non-NAb) were present or if neutralizing antibodies (-NAb) were present.

Figure 7:
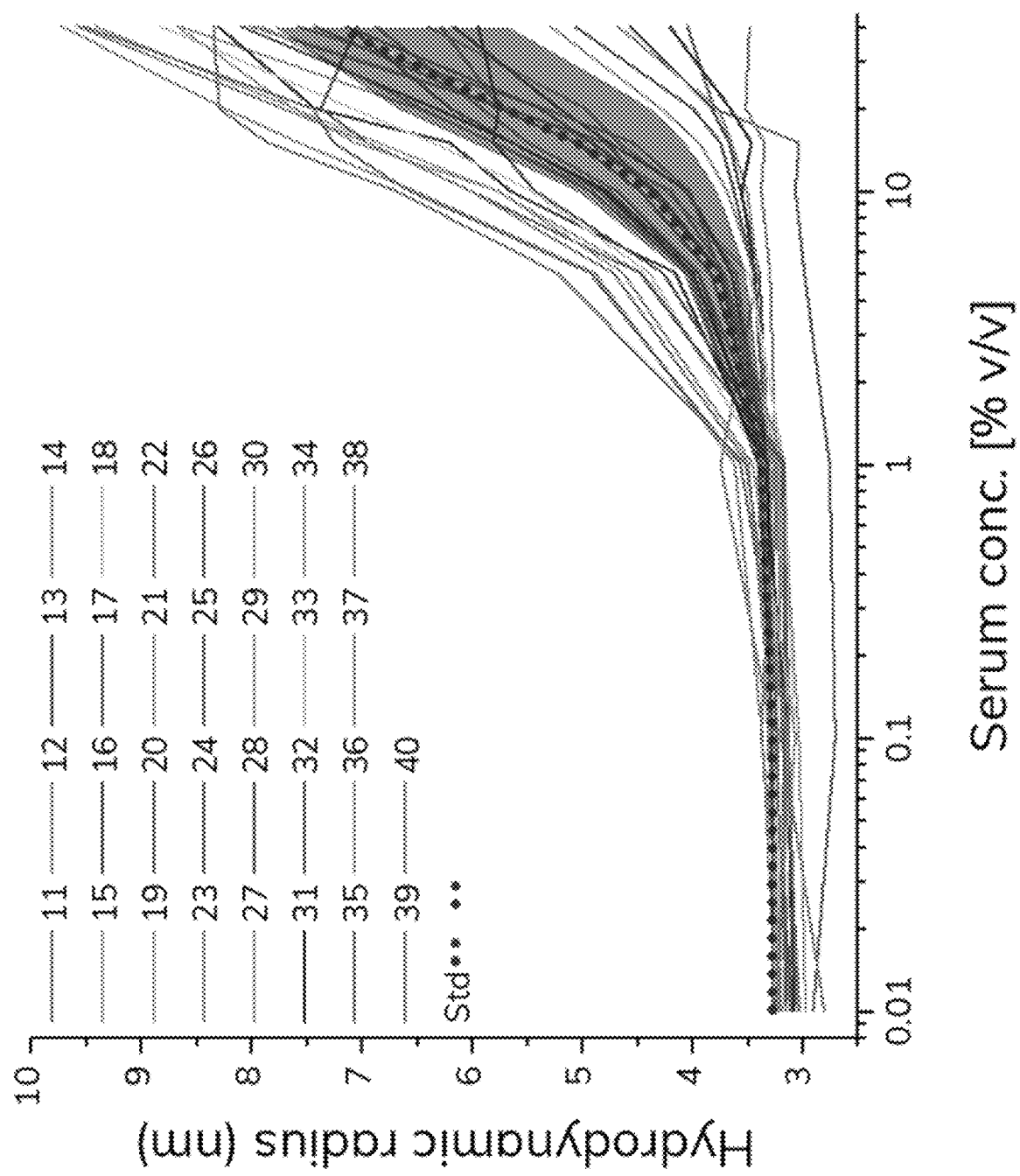

FIG. 7 shows the hydrodynamic radius of TNF-α-AF488 (100 nM) alone+complexes thereof as a function of serum concentration (0-40% v/v) of the patients 11-40. The dotted line shows the benchmark values using the standard curve in 20% v/v plasma. The gray zone indicates 50% deviation in steady-state serum concentration of 8 μg/ml (~54 nM) adalimumab.

Based on the results of the 30 patients (11-40) a drug response factor (DRF) for each patient were determined as the apparent Kd value. The goodness of fit was based on the measurement pertaining to a given patient and is a measure of how well the measurement fits the binding model. The normalized drug response factors (DRFnorm), was determined as the ratio of the DRF and the benchmark DRF (normal response).

As seen in FIG. 8, patients classified as NAb positive, normal responders, and non-NAb positive can be identified.

Figure 9:
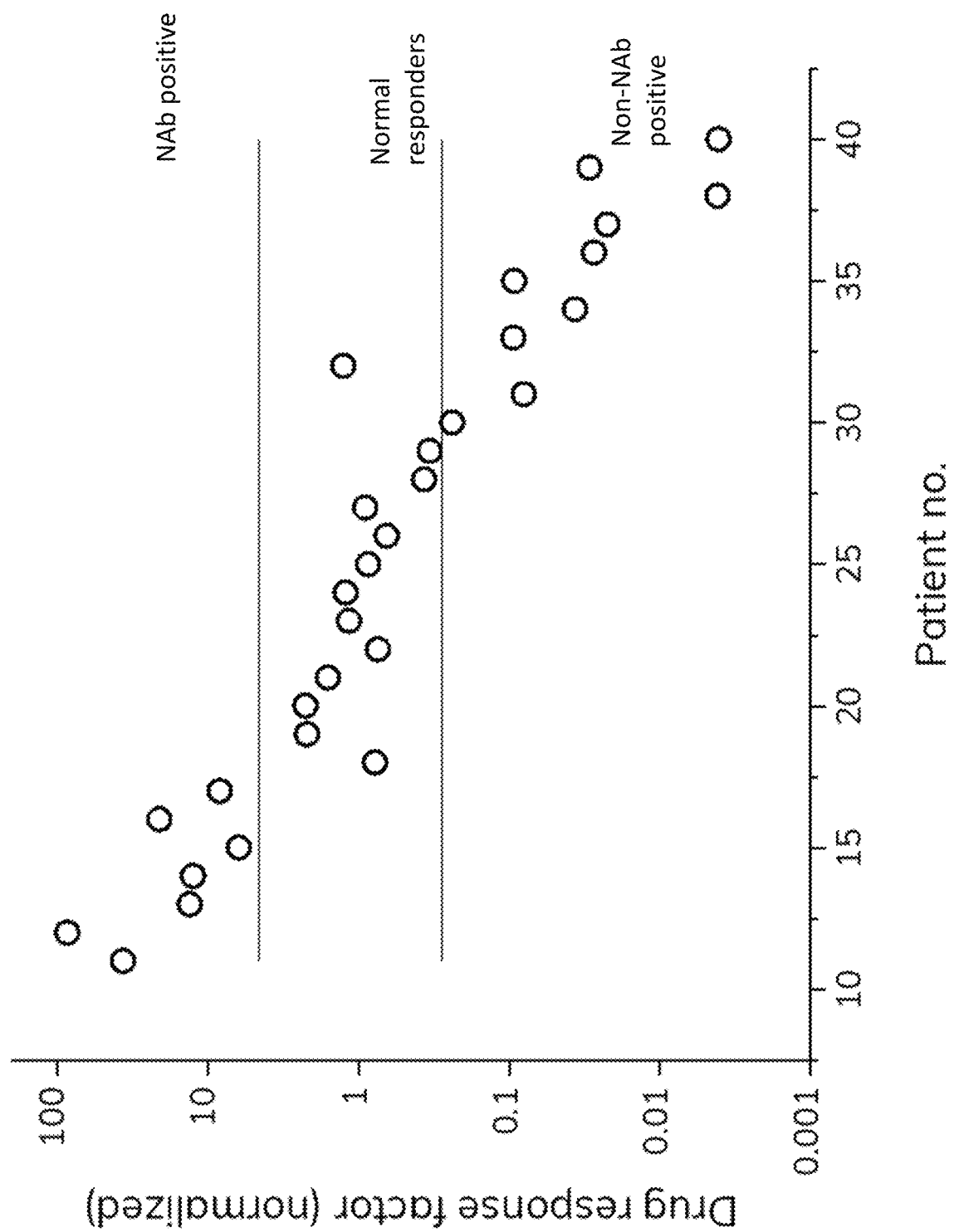
FIG. 9 shows the distribution of normalized drug response factor (DRFNorm) for the experimental group (30 patients).

FIG. 9 shows Distribution of normalized drug response factor (DRFNorm) for the experimental group (30 patients).

Example 1b

Example 1b is similar to example 1a, the only difference is that a different injection process is used. Here, the labeled TNF-α and the patient serum are mixed in the capillary.

Figure 4:
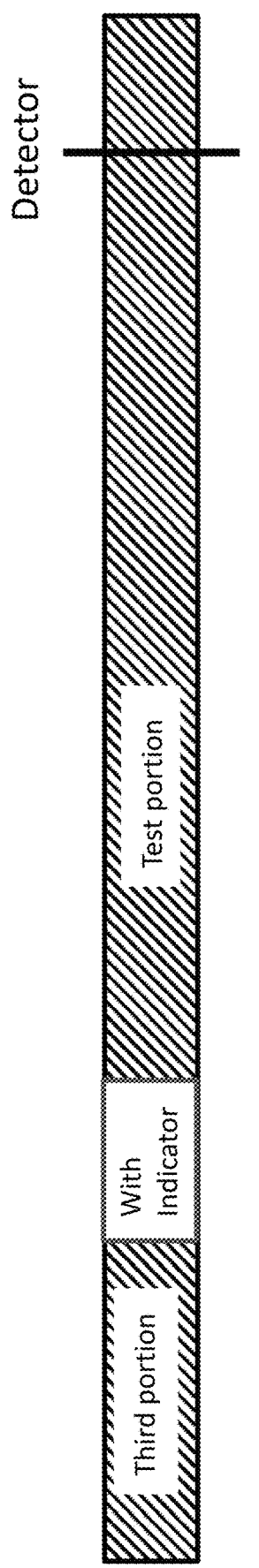
FIG. 4 illustrates the injection process used in example 1b.

The injection process is illustrated in FIG. 4.

A first portion of the prepared sample, which in this example is the test portion, was filled into the capillary at 3500 mbar for 20-25 s followed by injection of a second portion of buffer with the indicator (TNF-α-AF488 in a concentration of 100 nM). Lastly, the previously injected portions including the test portion were mobilized to the fluorescence detector with a third portion of the prepared sample at 400 mbar for 180-240 s.

The injection protocol in FIG. 3 allows to probe the association kinetics. For fast association kinetics the result will be similar to example 1a. However, example 1b has the additional advantage of very limited sample preparation.

Example 1c

Example 1c is similar to example 1a, the only difference is that a different injection process is used. Here, the labeled TNF-α and the prepared test portion are pre-mixed and injected in the capillary. However, the capillary is not filled with prepared sample as in 1a and 1b. Instead a buffer solution is used to mobilized the sample. The injection process is illustrated in FIG. 5.

A portion of buffer was filled into the capillary at 3500 mbar for 20-25 s followed by injection at 50 mbar for 10 s of a test portion of the prepared sample into which the indicator (TNF-α-AF488 in a concentration of 100 nM) had been mixed. Lastly, the previously injected portions including the test portion were mobilized to the fluorescence detector with a portion of buffer at 400 mbar for 180-240 s.

Figure 5:
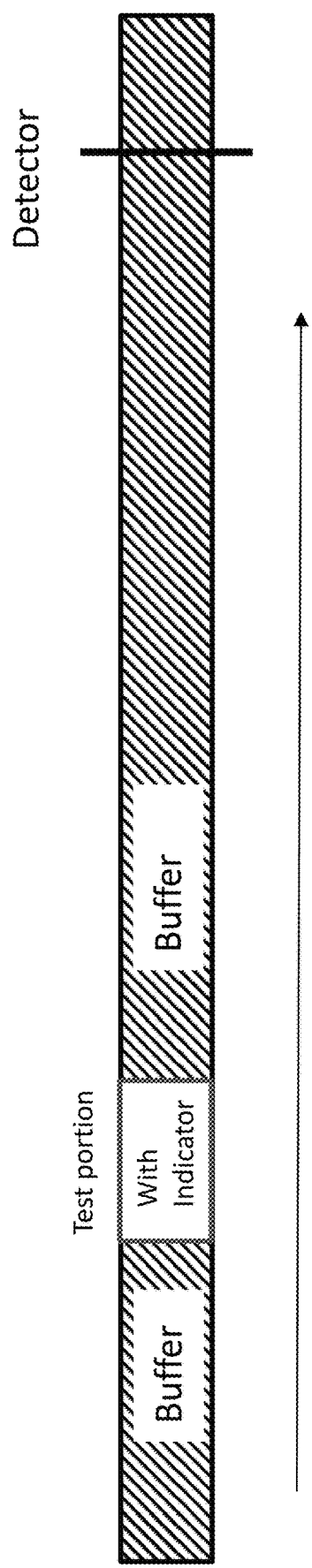
FIG. 5 illustrates the injection process used in example 1c.

The injection protocol in FIG. 5 allows to probe the dissociation kinetics of the complex.

Example 2

The FIDA methodology is "first principle" allowing response to be calculated. A "normal" response and drug activity can thus be calculated with prior knowledge of $K_d$'s and sizes of target (indicator) and complex. The size of indicator and complexes can for example be calculated from PDB files with atomic coordinates.

Example 3

Example 1 can be performed using any soluble drug target and biopharmaceutical. In case the drug target is a membrane protein it may be advantageous to use nanodiscs or detergents/lipids to solubilize the protein.

Example 4

Immune Response to Virus Infection.

Here the target is a surface protein on the virus. Otherwise, the example is carried out as example 1. The two outcomes are not-infected "non-binding region" showing no antibodies against the virus surface protein and a region of sizes corresponding to binding to viral auto antibodies.

Example 5

Immune Response to Vaccination.

This example is similar to example 4, but with artificial vaccine protein. The vaccine protein could be a surface protein on the vaccine, or a protein produced by the patient as a part of the vaccination.

Example 6

Measuring Neutralizing Ability of Auto-Antibodies.

Here the target is the fluorescently labeled virus surface protein (or part of it) and the endogenous cell surface receptor is the acceptor. The indicator and acceptor is added to patient serum to form the indicator sample. The acceptor sample is composed of patient serum and the acceptor. Serum titrations are performed as in example 1 (indicator concentration is kept constant and acceptor is varied in the patient serum dilutions. Binding (non-neutralizing) antibodies will show larger complex sizes than expected (as in example 1), whereas neutralizing antibodies will result in no binding or disruption of binding (as in example 1).

Example 7

In this example the assays in example 6 is reversed so that the virus surface protein is the analyte and the indicator fluorescently labeled endogenous cell surface receptor.

Example 8

Correcting for Endogenous Presence of Target.

In some cases, it will be needed to take into account the presence of non-labeled endogenous target. This can be done by adjusting the labeled target concentration in the calculation by simply adding the concentration of the endogenous target.

Example 9

Immunological Diseases

Immune response and auto-antibodies to self-antigens (e.g., protein, DNA, etc.). Here the target is a self-antigen. Otherwise, the example is carried out as example 1. The two outcomes are "no immune response/non-binding region" showing no antibodies against the self-antigen and a region of sizes corresponding to binding to self-antigens (immune response).

The invention claimed is:

1. A method of determining an immunogenic response characteristic of a chemical substance in a biological fluid, the method comprising:
   obtaining a sample of the biological fluid comprising the chemical substance;
   providing at least one prepared sample from at least a portion of the sample;
   for each prepared sample, bringing at least a test portion of the prepared sample into a laminar flow in a channel and providing that the prepared sample is in contact with a binding partner for the chemical substance, wherein the binding partner comprises an optical marker and a molecule or group of molecules selected from the group consisting of a molecule identical to a target for the chemical substance, a target analog, and a molecule or complex comprising at least one binding site for the chemical substance identical to or corresponding to the target for the chemical substance;
   performing at least one read out of the optical marker comprising reading out a concentration profile of the optical marker at a detection location of the channel;
   determining a characteristic flow parameter of the marked binding partner in contact with the prepared sample based on said at least one read out of the optical marker, wherein the characteristic flow parameter is selected from the group consisting of a dispersion parameter and a diffusion parameter;
   comparing the determined characteristic flow parameter with at least one reference value representing a non-immunogenic response or a classification of non-immunogenic responses; and
   determining the immunogenic response characteristic of the chemical substance, comprising determining if the immunogenic response characteristic is indicative for a non-immunogenic response, an immunogenic response involving generated neutralizing antibodies (NAb) or an immunogenic response involving generated non-neutralizing antibodies (non-Nab).

2. The method of claim 1, wherein the sample is a sample from an individual mammal and wherein the sample is selected from the group consisting of extracellular fluid, intracellular fluid, blood, urine, semen (seminal fluid), vaginal secretions, cerebrospinal fluid (CSF), synovial fluid, pleural fluid (pleural lavage), pericardial fluid, peritoneal fluid, amniotic fluid, saliva, nasal fluid, mucus, optic fluid, gastric fluid, breast milk, cell culture fluid or any combinations thereof.

3. The method of claim 1, wherein the chemical substance comprises a biopharmaceutical selected from the group consisting of cytokines, antibodies, enzymes, hormones, immune modulators and vaccine proteins.

4. The method of claim 1, wherein the chemical substance is an active agent for treatment of at least one of cancers, cardiovascular diseases, metabolic diseases or neurodegenerative diseases.

5. The method of claim 1, wherein the characteristic flow parameter comprises a weighted average dispersion of the marked binding partner and complexes comprising the marked binding partner.

6. The method of claim 1, wherein the determination of the characteristic flow parameter is performed by a method comprising subjecting the test portion of the at least one prepared sample and at least one support liquid to a laminar flow in a common channel, wherein the test portion is in interfacial contact with the support liquid, detecting a concentration profile of the optical marker and determine the characteristic flow parameter.

7. The method of claim 1, wherein the provision of at least one prepared sample from the sample comprises providing a plurality of prepared samples from the sample by adding a buffer system, wherein the respective prepared sample are provided to have different concentration of the sample.

8. The method of claim 6, wherein the at least one support liquid comprises a buffer system and wherein the binding partner for the chemical substance is added to at least one of the test portion and the support liquid prior to subjecting the test portion and the support liquid to the laminar flow in the common channel.

9. The method of claim 1, wherein the determination of the characteristic flow parameter is performed by a method comprising subjecting the test portion of the at least one prepared sample and at least one support liquid to a laminar flow in a common channel, wherein the test portion is in interfacial contact with the support liquid, comprising feeding a first portion of the support liquid into the common channel, feeding the test portion into the common channel to be in interfacial contact with the first portion of the support liquid and feeding a second portion of the support liquid into the common channel to be in interfacial contact with the test portion and subjection the portions to the laminar flow, detecting a concentration profile of the optical marker and determine the characteristic flow parameter.

10. The method of claim 1, wherein the reading out of the concentration profile of the marker is performed at the detection location of the channel while the test portion and the support liquid are in laminar flow in the channel at the detection location.

11. The method of claim 1, wherein the at least one reference value comprises one or more reference values obtained from previous determinations performed on one or more samples of the biological fluid from individuals with a non-immunogenic response.

12. The method of claim 1, wherein the at least one reference value comprises one or more calculated reference values, based on one or more of molecular size of the chemical substance, molecular size of the marked binding partner, equilibrium dissociation constant for the chemical substance and marked binding partner, dispersion of the marked binding partner, dispersion of a complex comprising the marked binding partner and the chemical substance, the viscosity of the prepared sample and/or the viscosity of the support liquid.

13. The method of claim 1, wherein the at least one reference value comprises one or more reference values, each provided by a response factor classification associated to a selected concentration of the sample or a selected concentration of chemical substance, wherein the response factor classification comprises an indication of a factor range indicating a non-immunogenic response, a factor range indicating an immunogenic response comprising formation of neutralizing antibodies (NAb) and/or a factor range indicating an immunogenic response comprising formation of non-neutralizing antibodies (non-NAb).

14. The method of claim 1, wherein the sample is a sample obtained from an individual subjected to treatment with the chemical substance according to a drug administration program and wherein the determined immunogenic response characteristic is indicative for a response of the treatment and wherein the determined response characteristic is indicative for, if the response of the treatment involves formation of Anti-Drug-Antibody (ADA), for the level of ADA generation and if the treatment involves formation of neutralizing antibodies (NAb) or of non-neutralizing antibodies (non-NAb), and wherein the method comprises classifying the determined immunogenic response as a non-immunogenic response, an immunogenic response comprising formation of neutralizing antibodies (NAb) or an immunogenic response comprising formation of non-neutralizing antibodies (non-NAb).

15. A method of determining an immunogenic response characteristic of a drug candidate in a cell culture, the method comprising:
  performing an in vitro test of the drug candidate, wherein the drug candidate is a drug candidate for treatment of a medical condition involving a target molecule;
  subjecting the cell culture comprising said target with the drug candidate according to a selected program by subjecting the cell culture to a selected concentration of the drug candidate at least one time;
  obtaining a sample of the cell culture;
  providing at least one prepared sample from at least a portion of the sample;
  for each prepared sample, bringing a test portion of the prepared sample into a laminar flow in a channel, and providing that the prepared sample is in contact with a binding partner for the drug candidate, wherein the binding partner comprises an optical marker and a molecule or group of molecules selected from the group consisting of a molecule identical to a target for the drug candidate, a target analog, and a molecule or complex comprising at least one binding site for the drug candidate identical to or corresponding to the target for the drug candidate;
  performing at least one read out of the optical marker comprising reading out a concentration profile of the optical marker at a detection location of the channel;

determining a characteristic flow parameter of the marked binding partner in contact with the prepared sample based on said at least one read out of the optical marker, wherein the characteristic flow parameter is selected from the group consisting of a dispersion parameter and a diffusion parameter;

comparing the determined characteristic flow parameter with at least one reference value representing a non-immunogenic response or a classification of non-immunogenic responses; and determining the immunogenic response characteristic of the drug candidate, comprising determining if the immunogenic response characteristic is indicative for a non-immunogenic response, an immunogenic response involving generated neutralizing antibodies (NAb) or an immunogenic response involving generated non-neutralizing antibodies (non-Nab).

16. The method of claim 15, wherein the provision of the prepared sample of each drug candidate comprises adding buffer system to a selected concentration of the sample or of the drug candidate and wherein the step of comparing the determined characteristic flow parameter with a respective reference value and determining the immunogenic response characteristic of the drug candidate for the drug candidate(s) comprises comparing the determined characteristic flow parameter with response factor classification associated to said selected concentration of the sample or of the drug candidate and classifying the determined immunogenic response as a non-immunogenic response, an immunogenic response comprising formation of neutralizing antibodies (NAb) or an immunogenic response comprising formation of non-neutralizing antibodies (non-NAb).

17. The method of claim 15, wherein the drug candidate is a drug candidate for development of a drug for treatment of a disease selected from cancers, cardiovascular diseases, metabolic diseases or neurodegenerative diseases.

18. The method of claim 15, wherein the drug candidate is a drug candidate for treatment of a condition of an individual and the cell culture is a cell culture of said individual.

19. The method of claim 1, wherein the chemical substance in the biological fluid is obtained from an individual or a cell culture subjected to the chemical substance.

* * * * *